(12) United States Patent
Ooya et al.

(10) Patent No.: US 8,603,982 B2
(45) Date of Patent: *Dec. 10, 2013

(54) MEDICAL COMPOSITION

(75) Inventors: Shouji Ooya, Ashigarakami-gun (JP); Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 239 days.

This patent is subject to a terminal disclaimer.

(21) Appl. No.: 12/935,551

(22) PCT Filed: Mar. 30, 2009

(86) PCT No.: PCT/JP2009/001451
§ 371 (c)(1),
(2), (4) Date: Sep. 29, 2010

(87) PCT Pub. No.: WO2009/122710
PCT Pub. Date: Oct. 8, 2009

(65) Prior Publication Data
US 2011/0028396 A1    Feb. 3, 2011

(30) Foreign Application Priority Data

Mar. 31, 2008   (JP) ................. 2008-090011

(51) Int. Cl.
*A61K 38/00* (2006.01)
*A61K 38/36* (2006.01)
*A61K 38/38* (2006.01)
*A61K 38/39* (2006.01)

(52) U.S. Cl.
USPC .......... 514/17.2; 514/1.1; 514/13.6; 514/15.2

(58) Field of Classification Search
None
See application file for complete search history.

(56) References Cited

U.S. PATENT DOCUMENTS

| 2006/0204441 A1* | 9/2006 | Atala et al. ...................... 424/9.6 |
| 2007/0128420 A1 | 6/2007 | Maghribi |
| 2010/0028691 A1* | 2/2010 | Ooya et al. ................. 428/423.1 |

FOREIGN PATENT DOCUMENTS

| JP | 63-115564 A | 5/1988 |
| JP | 02-147065 A | 6/1990 |
| JP | 10-016053 A | 1/1998 |
| JP | 2002-291862 A | 10/2002 |
| JP | 2005-213449 A | 8/2005 |
| JP | 2007-222600 A | 9/2007 |
| JP | 2007-301213 A | 11/2007 |
| JP | 2008-284256 | * 11/2008 ............. A61L 24/00 |
| JP | 2009-005995 A | 1/2009 |
| WO | 2008/026644 A1 | 3/2008 |
| WO | 2008/072378 A1 | 6/2008 |

OTHER PUBLICATIONS

Takagi Makoto et al, machine translation of JP 2007-301213, enclosed. Nov. 22, 2007 publication date.*
Machine translation of JP 2008-284256 (2008). Translated Dec. 10, 2012.*
International Preliminary Report on Patentability dated Dec. 23, 2010 on International Application No. PCT/JP2009/001451.
Office Action dated Jun. 18, 2013 in Japanese Application No. 2010-505385.

* cited by examiner

*Primary Examiner* — Julie Ha
(74) *Attorney, Agent, or Firm* — Sughrue Mion, PLLC

(57) ABSTRACT

A medical composition is described in which a synthetic polymer substrate and a composition mainly composed of a biopolymer directly adhere to each other due to dissolution of the surfaces thereof. The medical composition allows one to attach a biopolymer composition to a synthetic polymer substrate without the use of a toxic adhesive.

11 Claims, No Drawings

MEDICAL COMPOSITION

TECHNICAL FIELD

The present invention relates to a medical composition obtained by attaching a composition mainly composed of a biopolymer to a synthetic polymer substrate.

BACKGROUND ART

In recent years, biopolymers represented by collagen and gelatin have been used in the field of regenerative medicine which has been energetically studied at home and abroad. For instance, it has been shown that ischemic disease lesions can be significantly improved by embedding a gelatin composition comprising a gelatin sponge (Patent Document 1) containing cell growth factors in such lesions on the legs or the chest and attaching such composition to defects on the skin surface.

Biopolymer sponges lack strength and promote bacterial growth, which are problematic. Therefore, it is necessary to reinforce or coat the above composition, depending on the diseases to which the composition is applied. For instance, in the case of skin ulcer treatment, a sponge containing growth factors is attached to the skin surface. As a result, the gelatin portion of the sponge is exposed to the exterior. In general, synthetic polymer supports are often used to reinforce or coat biopolymers.

Usually, synthetic polymers are less likely to adhere to biopolymers. Synthetic polymer cannot adhere to biopolymers by itself. For adhesion between synthetic polymers and biopolymers, adhesives are used. Alternatively, adhesion is achieved by physical suturing.

In general, most adhesives are poorly biocompatible. Therefore, when adhesives come into contact with biological tissues, inflammation or an allergic reaction might be induced. In addition, in the case of physical suturing, mechanical strains are concentrated on the suture, which might result in destruction of a composition at the suture site. Therefore, in the medical practice, a technique for attaching a medical composition to a synthetic polymer substrate with the use of a biopolymer, but not a toxic adhesive, has been awaited.

[Patent Document 1] JP Patent Publication (Kokai) No. 2005-213449 A

DISCLOSURE OF THE INVENTION

Problem to be Solved by the Invention

When a composition comprising a biopolymer is used for medical purposes, it is difficult to attach a biopolymer composition mainly composed of a synthetic polymer to a substrate. Therefore, a toxic adhesive is generally used. It is an object of the present invention to attach a biopolymer composition to a synthetic polymer substrate without the use of a toxic adhesive.

Means For Solving Problem

As a result of intensive studies in order to attain the above object, the present inventors found that it is possible to attach a biopolymer composition to the surface of a synthetic polymer substrate by dissolving the surfaces of both the synthetic polymer substrate and the biopolymer composition with the use of a solvent (e.g., an organic fluorine compound) capable of dissolving both and removing the solvent after the contact therebetween. This has led to the completion of the present invention.

Thus, the present invention provides a medical composition, wherein a synthetic polymer substrate and a composition mainly composed of a biopolymer directly adhere to each other due to dissolution of the surfaces thereof.

Preferably, the composition ratio of the synthetic polymer substrate and the composition percentage of the composition mainly composed of a biopolymer at the interface therebetween continuously vary.

Preferably, the biopolymer is a protein, a polysaccharide, or a derivative thereof.

Preferably, the protein is at least one member selected from the group consisting of collagen, gelatin, albumin, casein, fibroin, fibrin, laminin, fibronectin, and vitronectin.

Preferably, the protein is at least one member selected from the group consisting of collagen, gelatin, albumin, casein, and fibrin.

Preferably, the protein is gelatin.

Preferably, the polysaccharide is glycosaminoglycan, chitosan, or chitin.

Preferably, the biopolymer is crosslinked by heat, light, or a crosslinking agent.

Preferably, the synthetic polymer is polyethylene terephthalate, segmented polyurethane, polyurethane, polyvinyl alcohol, polyethylene, polylactic acid, polyglycolic acid, poly(ε-caprolactone), polyvinylpyrrolidone, or a copolymer thereof.

The present invention provides a method for producing the aforementioned medical composition of the present invention, which comprises the steps of: coating a synthetic polymer substrate with a solvent capable of dissolving both the synthetic polymer substrate and a composition mainly composed of a biopolymer; applying the composition mainly composed of a biopolymer to the portion coated with the solvent before removal of the solvent; and removing the solvent.

Preferably, the solvent is an organic fluorine compound.

Preferably, the organic fluorine compound is a compound having a carbon number of 2 to 8.

Preferably, the organic fluorine compound is a compound having a carbon number of 2 to 3.

Preferably, the organic fluorine compound is 1,1,1,3,3,3-hexafluoro-2-propanol, 2,2,2-trifluoroethanol, or hexafluoroacetone.

The present invention further provides the medical composition which is produced by the aforementioned method of the present invention.

Effects of the Invention

It is possible to attach a biopolymer composition to a synthetic polymer substrate without the use of a biologically toxic adhesive according to the present invention. That is to say, according to the present invention, a medical composition consisting of a highly biocompatible substrate can be provided.

BEST MODE FOR CARRYING OUT THE INVENTION

A biopolymer to be used in the present invention is not particularly limited, as long as it is a biologically derived polymer. It is preferably a protein, a polysaccharide (e.g., glycosaminoglycan or proteoglycan), or a derivative thereof More preferably, the biopolymer is collagen, gelatin, albumin, laminin, casein, fibroin, fibrin, chitin, chitosan, fibronectin, vitronectin, urokinase, thrombomodulin, antithrombin III, hyaluronic acid, hyaluronic acid ester (hyaluronate), heparin, or chondroitin sulfate. Further preferably, the biopolymer is collagen, gelatin, albumin, laminin, casein, fibroin, fibrin, fibronectin, or vitronectin. Particularly preferably, the biopolymer is collagen, gelatin, albumin, casein, fibroin, or chitosan. Most preferably, the biopolymer is collagen or gelatin. The protein origin is not particularly limited. Any human-, bovine-, pig-, or fish-derived proteins or gene recombinant proteins can be used. As a gene recombinant gelatin, those described in EU1014176A2 or U.S. Pat. No. 6,992,172 can be used, but the examples are not limited thereto. Also, the biopolymer may be partially hydrolyzed.

The form of the biopolymer is not particularly limited. However, the biopolymer may be in the form of a non-crosslinked product, a physically or chemically crosslinked product, a chemically modified product, or a mixture thereof. When the biopolymer is chemically modified, specific examples of such biopolymer include a biopolymer containing an ester bond, an amide bond or ether bond between the biopolymer and another compound.

In addition, it is not required that the biopolymer be present alone within a composite prepared with the use of the biopolymer, and the biopolymer may be contained as a part of a composite.

The form of a biopolymer is preferably a sponge-like composition. The term "sponge-like composition" used herein refers to a composition comprising the above biopolymer and preferably crosslinked gelatin and having many fine pores. When a sponge-like composition having a structure with many fine pores is used as a regenerative medicine substrate, cells that have been sowed on the composition enter fine pores and adhere to the pore surfaces, allowing three-dimensional spread of the cells. In addition, when the above composition containing no cells sowed therein is implanted, cells present in the vicinity of the implantation site can readily enter fine pores. Further, sufficient nutrition can be supplied to adhering cells, allowing normal cell proliferation and differentiation.

For the average pore size of fine pores of a gelatin sponge, the most appropriate value can be selected depending on tissues or organs to be regenerated as substrates for regenerative medicine. The lower limit is preferably 10 μm and the upper limit is preferably 500 μm. When the lower limit is less than 10 μm, cells cannot enter a gelatin sponge, resulting in significantly poor cell adhesiveness or insufficient three-dimensional spread of adhering cells. When the upper limit exceeds 500 μm, the cell density decreases, which might make it impossible to regenerate tissues or organs.

A method for producing a sponge-like composition comprising a biopolymer is not particularly limited. Such composition can be produced in a manner such that an aqueous gelatin solution is cooled so as to gel, followed by freezing and lyophilization. For example, the composition can be produced with the method described in JP Patent Publication (Kokai) No. 2005-213449 A or JP Patent Publication (Kokai) No. 2007-9185 A.

Preferably, a sponge-like composition comprising a biopolymer has a crosslinked structure. The above crosslinked gelatin can be obtained by crosslinking of gelatin. A crosslinking method is not particularly limited. Examples thereof include a vacuum heat dehydration method, a dry heat method, a γ-ray irradiation method, an ultraviolet irradiation method, an electron beam irradiation method, an X-ray irradiation method, and a method using a crosslinking agent. Of these, a method using a crosslinking agent is preferable because crosslinking can be carried out such that the entirety of a gelatin sponge has a uniform degree of crosslinking.

The above crosslinking agent is not particularly limited. Examples thereof include glutaraldehyde, formalin, ethylene glycol diglycidyl ether, polyethylene glycol diglycidyl ether, polyglycerol polyglycidyl ether, glycerol polyglycidyl ether, hexamethylene diisocyanate, 1-ethyl-3-(3-dimethylaminopropyl) carbodiimide hydrochloride (EDC or WSC), and dicyclohexylcarbodiimide (DCC). Preferably, glutaraldehyde is used.

A synthetic polymer to be used in the present invention is not particularly limited, as long as the present invention can be performed, and it is preferably a polymer soluble in an organic fluorine compound. The synthetic polymer is more preferably a polymer having a urethane bond, an ester bond, an ether bond or a carbonate bond, or a vinyl polymer, or a copolymer thereof. More preferably, the synthetic polymer is polyorthoester, polylactic acid, polyglycolic acid, or a copolymer thereof, poly(ε-caprolactone), polyurethane, segmented polyurethane, polyether polyurethane, or polyethylene terephthalate (PET). Further preferably, the synthetic polymer is poly(ε-caprolactone), polyurethane, segmented polyurethane, polyether polyurethane, or PET. The synthetic polymer may be contained as a component of a composite or contained in a mixture with other materials. The percentage by weight of the synthetic polymer in a composite is not particularly limited, as long as the present invention can be performed, and is substantially 10% or more, preferably 30% or more, more preferably 50% or more, and most preferably 80% or more.

The molecular weight of the synthetic polymer is not particularly limited and is generally 1 KDa or more and 10 MDa or less, preferably 5 KDa or more and 500 KDa or less, and most preferably 10 KDa or more and 100 KDa or less. Moreover, a synthetic polymer that may be used herein is one that has been subjected to crosslinking and/or chemical modification.

The form of the synthetic polymer is not particularly limited, as long as the present invention can be performed. Examples of the form include gel, sponge, film, non-woven fabric, fibers (tubes), and particles. The synthetic polymer can be used in any form. Examples of such form include pyramidal, conical, rectangular cylindrical, circular cylindrical, spherical, and spindle-shaped composites and composites produced using arbitrary molds with desired shapes. Preferably, the form is a rectangular cylindrical, circular cylindrical, or spindle-shaped composite or a composite produced using a mold with a desired shape. More preferably, the form is a pyramidal, conical, rectangular cylindrical, or circular cylindrical composite. Most preferably, the form is a rectangular cylindrical or circular cylindrical composite. For example, when an artificial vascular lumen surface is coated with albumin, an HFIP solution containing albumin is added into a PET tube and then the tube can be coated and dried via rotation of the tube.

The size of the composite comprising the synthetic polymer is not particularly limited. However, when the composite is in the form of gel, sponge, or non-woven fabric, the size thereof is preferably 500 centimeters square or less, preferably 100 centimeters square or less, particularly preferably 50 centimeters square or less, and most preferably 10 centimeters square or less. When it is formed into a fiber (tube), the diameter of a fiber or tube (or one side of the cross section thereof) is 1 nm or more and 10 cm or less, preferably 1 nm or more and to 1 cm or less, more preferably 1 nm or more and 100 μm or less, particularly preferably 1 nm or more and 1 μm or less, and most preferably 1 nm or more and 10 nm or less.

In addition, the length thereof is not particularly limited. The length thereof is preferably 10 μm or more and 100 m or less, more preferably 100 μm or more and 10 m or less, further preferably 1 mm or more and 1 m or less, and most preferably 1 cm or more and 30 cm or less. When the composition is in the form of particles, the particle size (diameter) preferably ranges from 1 nm to 1 mm, more preferably ranges from 10 nm to 200 μm, further preferably ranges from 50 nm to 100 μm, and particularly preferably ranges from 100 nm to 10 μm.

The thickness of a composite comprising the synthetic polymer is not particularly limited. The thickness is preferably 1 nm or more, more preferably 10 nm or more, further preferably 100 nm or more, even more preferably 1 μm or more, yet more preferably 10 μm or more, and most preferably 100 μm or more.

The method for producing a medical composition of the present invention is characterized in that no adhesive is used therein. Specifically, the method for producing a medical composition of the present invention comprises the steps of: coating a synthetic polymer substrate with a solvent capable of dissolving both the synthetic polymer substrate and a composition mainly composed of a biopolymer; applying the composition mainly composed of a biopolymer to the portion coated with the solvent before removal of the solvent; and removing the solvent.

A solvent capable of dissolving a synthetic polymer substrate and a composition mainly composed of a biopolymer is preferably an organic fluorine compound. The type of an organic fluorine compound used herein is not particularly limited as long as a solvent can dissolve both a biopolymer and a synthetic polymer. However, the organic fluorine compound is preferably an organic fluorine compound having a carbon number of 1 to 8 (and more preferably a carbon number of 2 to 8), more preferably an organic fluorine compound having a carbon number of 1 to 6 (and more preferably a carbon number of 2 to 6), and particularly preferably an organic fluorine compound having a carbon number of 1 to 3 (and more preferably a carbon number of 2 to 3). In addition, an organic fluorine compound is preferably alcohol, ketone, or carboxylic acid. Specific examples of an organic fluorine compound include 1,1,1-hexafluoro-2-propanol (hereinafter sometimes referred to as HFIP), trifluoroethanol, hexafluoroacetone, trifluoroacetic acid, and perfluoropropionic acid. Most preferably, hexafluoro-2-propanol or trifluoroethanol is used. The organic fluorine compound may be used alone, or may be mixed with a solvent compatible to the organic fluorine compound and the mixture may be used. The compatible solvent is preferably water.

Specifically, the method of the present invention comprises the steps of: coating a synthetic polymer substrate with a solvent capable of dissolving both the synthetic polymer substrate and a composition mainly composed of a biopolymer; applying the composition mainly composed of a biopolymer to the portion coated with the solvent before removal of the solvent; and removing the solvent, so that the synthetic polymer is partially dissolved in the organic fluorine compound. Accordingly, the ratio of the biopolymer in comparison with that of the synthetic polymer continuously decreases in the adhesion portion relative to the depth from the composition surface. Specifically, according to the method of the present invention, it is possible to produce a composition comprising a synthetic polymer substrate and a composition mainly composed of a biopolymer that adhere to each other, which is a composition prepared by coating the surface of a synthetic polymer with a biopolymer, and in which the ratio of the biopolymer in comparison with that of the synthetic polymer continuously decreases in the adhesion portion depending on the depth from the composition surface. The composition having such structure is also within the scope of the present invention.

The composition mainly composed of a biopolymer of the present invention may contain a drug. Such drug is not particularly limited. Examples thereof include vitamins, anticancer agents, immunosuppressive agents, anti-inflammatory agents, antioxidants, antibacterial agents, antithrombotic agents, cytokines, nucleic acids, cosmetic components, and supplement components. Preferably, cytokines, nucleic acids, anticancer agents, and antibacterial agents can be used. These examples may contain known components. For example, a physiologically active substance that can bind to the composition mainly composed of a biopolymer of the present invention (e.g., a gelatin sponge) via electrostatic binding is not particularly limited as long as it is positively or negatively charged under physiological conditions. Examples thereof include: basic fibroblast growth factors (bFGFs); bone morphogenetic proteins (BMPs); epidermal growth factors (EGFs); cytokines such as IL-1α, IL-1β, IL-6, IL-8, TGF-α, TGF-β1, and TGF-β2; and other factors such as VEGF, IGF, HGF, MMPI, and PDGF (platelet-derived growth factor).

The present invention is hereafter described in greater detail with reference to the following examples, although the present invention is not limited thereto.

EXAMPLES

Example 1

Preparation of Protein Sponge

A PBS solution containing acid-treated gelatin of pig skin (100 mg, PSK gelatin, Nippi Inc.) and glutaraldehyde (GA) (0.9 mL; GA concentration: 0.1%) was introduced into a silicone mold (3 cm×3 cm) placed on a PET sheet. The solution was allowed to stand still at room temperature for 17 hours. Then, the mold was immersed in a largely excessive amount of an aqueous glycine solution (50 mM) and allowed to stand still therein at 37° C. for 1 hour. Subsequently, the resultant was allowed to stand still in water at 37° C. for 1 hour. The obtained gelatin gel was lyophilized so that a gelatin sponge was obtained.

It was possible to produce a similar sponge by the above method with the use of bovine serum albumin or casein instead of gelatin.

Example 2

Preparation of Protein Film

A 1,1,1,3,3,3-hexafluoro-2-propanol (HFIP) solution containing acid-treated gelatin of pig skin (100 mg) and glutaraldehyde (0.9 mL; GA concentration: 0.1%) was introduced (to a thickness of 1 mm) into a silicone mold (3 cm×3 cm) placed on a polypropylene sheet. The mold was allowed to stand still at room temperature for 17 hours. Then, the mold was immersed in a largely excessive amount of an aqueous glycine solution (50 mM) and allowed to stand still therein at 37° C. for 1 hour. Subsequently, the thus obtained film was allowed to stand still in water at 37° C. for 1 hour. The film was naturally dried so that a gelatin film was obtained.

It was possible to produce a similar film by the above method with the use of bovine serum albumin or casein instead of gelatin.

Example 3

Attachment of Protein Sponge To A Synthetic Substrate

HFIP and trifluoroethanol (TFE) were added dropwise to a PET film (surface area: 1 cm×1 cm; amount: 20 μL). The gelatin sponge or film prepared in Example 1 or 2 was placed on the film surface and allowed to stand still for 5 minutes. Subsequently, the film was placed in a humidifier/dryer (temperature: 50° C.; humidity: 100%) and allowed to stand still overnight, followed by natural drying for 1 day.

Meanwhile, different solvents (dimethylsulfoxide (DMSO), tetrahydrofuran, acetone, ethanol, and water) were separately added dropwise to PET films (surface area: 1 cm×1 cm; amount: 20 μL). The gelatin sponge or film prepared in Example 1 or 2 was placed on each film surface and allowed to sand still for 5 minutes. Subsequently, the films were placed in a humidifier/dryer (temperature: 50° C.; humidity: 100%) and allowed to stand still overnight, followed by natural drying for 1 day.

In cases of using HFIP or TFE, both the gelatin sponge and the gelatin film were found to strongly adhere to the PET film surfaces. Meanwhile, in cases of using tetrahydrofuran, acetone, ethanol, or water, no adhesion was observed regardless of the gelatin form, and the gelatin film or sponge immediately fell off from the film surface. In case of using DMSO, the gelatin film or sponge did not adhere to the PET film. In addition, it was impossible to remove the solvent used because of the high boiling point.

Therefore, it can be said that a gelatin composition was allowed to adhere to the PET surface without the use of an adhesive by using HFIP and TFE and then removing the solvents in order to allow a composition comprising gelatin to adhere to the PET surface.

Similar results were obtained by using albumin or casein instead of gelatin.

The invention claimed is:

1. A method for producing a medical composition wherein a synthetic polymer substrate and a sponge or film composition comprising a biopolymer are directly adhering to each other due to dissolution of the surfaces thereof, further comprising the steps of: coating a synthetic polymer substrate with a solvent which dissolves both the synthetic polymer substrate and a composition comprising a biopolymer; applying the sponge or film composition comprising a biopolymer to the portion coated with the solvent before removal of the solvent; and removing the solvent, wherein the solvent is an organic fluorine compound.

2. The method according to claim 1, wherein the organic fluorine compound is a compound having a carbon number of 2 to 8.

3. The method according to claim 1, wherein the organic fluorine compound is a compound having a carbon number of 2 to 3.

4. The method according to claim 1, wherein the organic fluorine compound is 1,1,1,3,3,3-hexafluoro-2-propanol, 2,2,2-trifluoroethanol, or hexafluoroacetone.

5. The method according to claim 1, wherein the biopolymer is a protein or a polysaccharide.

6. The method according to claim 1, wherein the biopolymer is a protein which is at least one member selected from the group consisting of collagen, gelatin, albumin, casein, fibroin, fibrin, laminin, fibronectin, and vitronectin.

7. The method according to claim 6, wherein the protein is gelatin.

8. The method according to claim 1, comprising crosslinking the biopolymer with heat, light, or a crosslinking agent.

9. The method according to claim 1, wherein the synthetic polymer is polyethylene terephthalate, segmented polyurethane, polyurethane, polyvinyl alcohol, polyethylene, polylactic acid, polyglycolic acid, poly(ε-capolactone), polyvinylpyrrolidone, or a copolymer thereof.

10. The method according to claim 1, wherein the solvent is 1,1,1,3,3,3-hexafluoro-2-propanol or 2,2,2-trifluoroethanol; the biopolymer is a protein which is at least one member selected from the group consisting of gelatin, albumin and casein; and the synthetic polymer is polyethylene terephthalate.

11. A medical composition, wherein a synthetic polymer substrate and a composition comprising a biopolymer are directly adhering to each other due to dissolution of the surfaces thereof, which is produced by the method according to claim 1.

\* \* \* \* \*